United States Patent [19]

Manner

[11] Patent Number: 4,714,785

[45] Date of Patent: Dec. 22, 1987

[54] METHOD FOR CONVERTING ORGANIC CHLOROFORMATE TO THE CORRESPONDING ORGANIC CHLORIDE

[75] Inventor: James A. Manner, Akron, Ohio

[73] Assignee: PPG Industries, Inc., Pittsburgh, Pa.

[21] Appl. No.: 907,246

[22] Filed: Sep. 15, 1986

[51] Int. Cl.$^4$ .................. C07C 41/01; C07C 19/02; C07C 17/00

[52] U.S. Cl. ........................ 568/614; 568/606; 568/608; 568/610; 568/655; 568/669; 568/681; 570/101; 570/186; 570/181; 570/201

[58] Field of Search .............. 568/606, 608, 610, 614, 568/655, 669, 681; 570/101, 201, 186, 181

[56] References Cited

U.S. PATENT DOCUMENTS 4,622,431  11/1986  Briody et al. ..................... 568/6

OTHER PUBLICATIONS

Rearrangement Occurring During Thermal Decomposition of Alkyl Chloroformates, P. W. Clinch, et al., J. Chem. Soc. B, pp. 747-751 (1971)(4).

The Chemistry of Chloroformates, M. Matzner et al., Chem. Rev. 64, pp. 645-661 and 677-687 (1964).

The Chemistry of Acyl Halides, S. Patai, Ed., Interscience Publishers, Chap. 12 by D. N. Kevill, pp. 381-399, 407-425, 446-453 (1972).

*Primary Examiner*—Howard T. Mars
*Attorney, Agent, or Firm*—Irwin M. Stein

[57] ABSTRACT

Organic haloformate, e.g., chloroformate, compounds are converted to their corresponding halides, e.g., chlorides, by heating the haloformate, e.g., between 90° C. and 150° C., in the presence of a catalytic amount of a carbon catalyst for a time sufficient to convert the haloformate to the corresponding halide.

12 Claims, No Drawings

METHOD FOR CONVERTING ORGANIC CHLOROFORMATE TO THE CORRESPONDING ORGANIC CHLORIDE

DESCRIPTION OF THE INVENTION

A variety of organic sulfonate compounds are used commercially as surfactants. One method that has been described for producing such surfactants involves the reaction of the chlorine-capped precursor compound with sodium sulfite. See, for example, U.S. Pat. No. 2,115,192. The chlorine capped precursor compound has been prepared by chlorinating the corresponding alcohol with phosphorus trichloride or thionyl chloride. When phosphorus trichloride is used as the chlorinating agent, difficulties in separating by-products, such as phosphorous acid, from the resulting principal chloride product are experienced. Thionyl chloride is economically unattractive as a chlorinating agent because it is a highly corrosive material. Moreover, it produces sulfur dioxide as a by-product of the chlorination reaction.

Phosgenation of alcohol precursors corresponding to the organic portion of the organic sulfonate surfactant and conversion of the resulting chloroformate to the chloride also can be used to prepare the chlorine capped precursor. However, converting the chloroformate to the corresponding chloride by a process which gives high yields of chloride product of acceptable color and minor amounts of by-products at reasonable cost has been difficult to achieve.

It has now been found that conversion of organic haloformates, e.g., chloroformates and bromoformates, to the corresponding halide compound, e.g., chloride and bromide, can be achieved readily and economically. In the process described hereinafter, organic haloformate is converted to the corresponding halide by heating the haloformate in the presence of a catalytic amount of a carbon catalyst for a time sufficient to achieve the foregoing conversion. In particular, the corresponding halide, e.g., chloride, compound derived from the organic haloformate compound, especially organic chloroformate compounds useful as intermediates in the preparation of anionic surfactant materials, are obtained by heating the haloformate at between about 90° C. and 150° C. in the presence of a catalytic amount of an activated carbon catalyst for between about 0.5 and 6 hours. Preferably, the conversion is performed in the substantial absence of water, e.g., under anhydrous conditions, and in the absence of a solvent for the organic haloformate. Use of the aforedescribed process permits preparation of a product that has an acceptable color and that is at least about 95 weight percent, preferably at least 98 weight percent, of the corresponding halide. By-product carbon dioxide generated during decomposition of the chloroformate is also readily removed from the reaction medium and liquid reaction product as a gas.

DETAILED DESCRIPTION OF THE INVENTION

Activated carbon catalysts are readily available commercially. Such materials may be used to catalyze the decomposition of the organic haloformate described herein to its corresponding organic halide. The carbon catalyst may have a surface area ranging from about 300 to 2000 square meters per gram and can vary in physical form from a powdery material to a dense granule or pellet. Preferably, the activated carbon catalyst is of a density such that it is readily separated from the liquid reaction product mixture by conventional solid-liquid separation techniques, e.g., filtration, centrifugation, etc. If the catalyst is too light and powdery, it may be difficult to separate economically.

It is contemplated that the catalyst may be used continuously until its catalytic activity decreases. Thereafter, the catalyst may be regenerated by washing the catalyst, usually with water, and then heating the washed catalyst in a furnace in the substantial absence of oxygen, e.g., by use of an inert gas atmosphere, to voltalize organic materials adsorbed by the catalyst. Thus treated catalyst can be screened and recycled for subsequent reuse in the process.

The amount of carbon catalyst that is added to the organic haloformate to effect conversion to the corresponding halide may vary. Generally, reaction rates will increase with increasing amounts of catalyst and with increasing conversion temperature. Commonly, only that amount of the catalyst which is sufficient to catalyze the decomposition of the organic haloformate, e.g., chloroformate, to the corresponding halide, e.g., chloride, at satisfactory rates of reaction will be used, i.e., a catalytic amount. In particular, the amount of carbon catalyst used may vary between about 0.5 and about 5 weight percent, e.g., between about 1 and about 3 weight percent, based on the weight of the organic haloformate reactant.

In accordance with the process of the present invention, the organic haloformate, e.g., chloroformate, compound is brought into contact with the carbon catalyst and heated for a time sufficient to convert substantially all of the haloformate, e.g., chloroformate, compound to the corresponding halide, e.g., chloride. The process is preferably carried out in the absence of a solvent for the organic haloformate to eliminate competing solvolysis reactions. Preferably, the process is conducted also in the substantial absence of water, i.e., under substantially anhydrous conditions, since the haloformate will hydrolyze in the presence of water to form a carbonate by-product, thereby reducing the yield of and contaminating the halide product.

The temperatures at which the aforesaid conversion occurs will vary depending on the organic haloformate compound; but, will typically be in the range of between about 90° C. and about 140° C. or 150° C., e.g., between about 100° C. and 120° C. or 140° C. The conversion may be accomplished at ambient pressures, although superatmospheric and subatmospheric pressures may be utilized. Heating of the organic haloformate compound is carried out for a time sufficient to convert substantially all, e.g., at least 95, preferably at least 98, and, most preferably, 100 weight percent of the haloformate to the corresponding halide. The time required to accomplish such substantial conversion will vary and depend on the haloformate compound employed, the amount of catalyst, and the temperatures used for the conversion. Generally, the higher the temperature used the shorter is the time required for the conversion reaction. Commonly, substantial conversion to the halide is accomplished in from about 0.5 to about 6 hours, e.g., between 1 and 3 hours.

If necessary, the liquid organic halide reaction product may be contacted with a suitable solid adsorbant, e.g., additional activated carbon, alumina, or silica, to improve the color of the product by removing contaminating traces of colored impurities that may be formed in the reaction mixture as a consequence of the decomposition of the organic haloformate. Generally, the carbon catalyst used in the present process will produce a halide product of little color, i.e., one that has a color, as measured by the APHA (American Public Health Association) scale, of less than about 250, usually less than 100. The color of the halide product produced by the process of the present invention will typically be nearly colorless. The APHA color scale employs a visual comparison against a series of standard colors. The comparison may be made against standard solutions or by use of a color chart, as used in the Hellige Aqua Tester (Model 611-A) sold by Hellige, Inc. Lower conversion temperatures tend to reduce the color of the halide product, but require a longer conversion time.

The process of the present invention is applicable to organic haloformate compounds, particularly organic chloroformate and bromoformate compounds. The present process is particularly and advantageously utilized for the conversion of organic haloformate compounds that are used as precursors of organic sulfonates (and salts thereof, e.g., the sodium, potassium, and lithium salts) that have found application as surfactants and in related fields of application. Examples of organic haloformate compounds to which the process of the present invention can be applied are organic haloformates of the general formula:

$$R_1(OR')_nOC(O)X$$

wherein X is halogen, e.g., chlorine and bromine, $R_1$ is selected from the group consisting of $C_1$-$C_{30}$ linear and branched alkyl, $C_5$-$C_6$ cycloalkyl, $C_1$-$C_4$ alkyl-substituted $C_5$-$C_6$ cycloalkyl, phenyl, alkyl substituted phenyl of the general formula, $(R_2)_bPh$—, wherein Ph is phenylene, $R_2$ is $C_1$-$C_{18}$ alkyl and b is an integer of from 1 to 3, phen($C_1$-$C_{18}$)alkyl, and $C_1$-$C_{18}$ alkyl-substituted phen($C_1$-$C_{18}$)alkyl having a total of from 7 to about 28 carbon atoms, R' is the substituted ethylene group, —$CH_2$—$CH(R'')$- wherein R'' is selected from hydrogen, methyl, ethyl and mixtures thereof, and n is a number from 0 to 40. Preferably, R' is the ethylene group, —$CH_2$—$CH_2$—. When $R_1$ is phenyl or alkyl substituted phenyl, n is at least 1. Treatment of the foregoing organic haloformate, e.g., chloroformate, compounds in accordance with the process of the present invention results in the preparation of the corresponding halide, e.g., chloride, compound, i.e., compounds of the graphic formula, $$R_1(OR')_nX$$

wherein $R_1$, R', X and n are as defined hereinabove. These organic halide compounds can be readily converted to the corresponding sulfonates by reaction of the halide with an alkali metal sulfite, e.g., sodium, potassium, lithium, or ammonium sulfite, as disclosed in U.S. Pat. No. 2,115,192. The sulfonation reaction is typically conducted at between 150° C. and 170° C. and pressures of between about 60 psi (413.7 kPa) and 115 psi (792.9 kPa) for about 16 to 20 hours. See, for example, U.S. Pat. No. 4,329,268.

As described in the above general formula, $R_1$ may be a $C_1$-$C_{30}$ branched or linear chain alkyl. This alkyl group is commonly derived from primary and secondary alcohols. $R_1$ may be derived from a single alcohol or a mixture of alcohols that are themselves derived from natural fats and oils or petroleum fractions. The particular alkyl or mixture of alkyls used will depend on the ultimate application to which the sulfonate end product is intended. For example, the number of carbon atoms comprising $R_1$ may range from 1 to 30 carbon atoms. A particularly useful alkyl range (or mixture of alkyls) is from 8 to 18 carbon atoms, e.g., from 11 or 12 to 15 carbon atoms. The mixture of alkyl groups in the alcohol precursor can vary and depends frequently on the particular manufacturer of the alcohol compounds from which the haloformate is derived.

The alkyl substituents of the alkyl substituted phenyl radicals will typically be a branched or straight chain hydrocarbon containing from 1 to 18 carbon atoms. The phenyl radical may contain from 1 to 3 of such alkyl substituents, more commonly 1 or 2 of such alkyl substituents. Similarly, the phen($C_1$-$C_{18}$)alkyl and $C_1$-$C_{18}$ alkyl substituted phen($C_1$-$C_{18}$)alkyl radicals will have from 1 to 18 carbon atoms in the alkyl portion(s) of the aforesaid radicals. With respect to the alkyl substituted phenalkyl radicals, the total number of carbon atoms in such radicals will commonly range from about 7 to 28 carbon atoms.

Alcohol precursor compounds containing polyoxyalkylene groups which comprise the organic haloformate are produced by reacting the corresponding alcohol with an alkylene oxide in the presence of a catalyst. The alkylene oxide can contain, for example, from 2 to 4 carbon atoms and is the precursor of the substituted ethylene group, —$CH_2$—$CH(R'')$—. More particularly, the alkylene oxide may be ethylene oxide, propylene oxide, or 1,2-butylene oxide. Also contemplated are compounds containing mixtures of alkylene groups, e.g., mixtures of ethylene oxide and propylene oxide, and propylene oxide and butylene oxide. The number of alkyleneoxy groups, i.e., "n" in the graphic formula, present in the compound can vary from 1 to about 40, more typically, "n" will vary between about 2 and about 20, e.g., 3 to 15. The number of alkylene oxide units present per mole of the aforedescribed organic molecule, is an average number and hence that number may be a fractional number between 1 and 40. Even though "n" is denoted as a number between 1 and 40, each organic molecule may contain a different number of alkylene oxide units with a distribution around the "n" value representing the average number of moles of alkylene oxide per mole of organic molecule. When n is 0, the haloformate compound contains no poly(alkylene oxide) groups.

Organic haloformate compounds described herein, e.g., organic chloroformates and bromoformates, may be prepared by reaction of the corresponding alcohol with the halogenating agents phosgene and bromophosgene (carbonyl bromide) respectively using techniques well know in the art for producing such materials, e.g., the chloroformates. The alcohol may be added to a pool of, for example, phosgene or the phosgene and alcohol added simultaneously to a reaction vessel. Preferably, the haloformate is the chloroformate.

Organic haloformate compounds described herein may be used as precursors of derivative sulfonate compounds, many of which are used as surfactants. Examples of such sulfonate materials are the alkane and aralkyl sulfonates, the sulfonated polyoxyalkylene alkyl phenols and ethoxylated and sulfonated alcohols generally. In accordance with one embodiment of the present process, the corresponding alcohol is reacted with phosgene to prepare the corresponding chloroformate, i.e., $R_1(OR')_nOC(O)Cl$, which is decomposed to the corresponding chloride, i.e., $R_1(OR')_nCl$. This chloride compound may subsequently be reacted with an alkali metal sulfite, e.g., sodium sulfite, to form the corresponding sulfonate compound, i.e., $R_1(OR')_nSO_3M$, wherein M is an alkali metal, e.g., sodium, lithium or potassium.

In accordance with a preferred embodiment of the present invention, liquid organic haloformate, e.g., chloroformate, compound is introduced into a nitrogen purged, dry reaction vessel containing stirring means. About 3 weight percent of activated carbon catalyst is also charged to the reaction vessel and the contents heated to between about 90 and 140° C. for about 1 to 6 hours. During the heating period, carbon dioxide is removed from the reaction vessel and forwarded to a scrubber and vent system to remove contaminants, e.g., hydrogen chloride and phosgene. Accordingly, the scrubber system should contain chemical means for scrubbing out acidic materials. Carbon dioxide removed from the reaction vessel may be scrubbed from the vent gas by reaction with a suitable hydroxy compound, e.g., lime, sodium hydroxide or barium hydroxide. The resulting liquid organic halide, e.g., chloride, reaction product may optionally be passed through a packed bed of alumina or carbon to remove color-producing impurities that may have been imparted to the reaction product during conversion of the haloformate.

In another embodiment of the present invention, it is contemplated that the catalytic amount of carbon may be added to the alcohol precursor of the haloformate, i.e., the alcohol having the general formula, $R_1(OR')_nOH$, wherein $R_1$, R' and n are as defined above, prior to conversion of the alcohol to the haloformate. Formation of the haloformate by simultaneous addition of, for example, phosgene and the corresponding precursor alcohol to the reaction vessel is performed at moderate temperatures, e.g., from about 23° C. to about 50° C. Following conversion of the alcohol to the haloformate, e.g., chloroformate, the reaction mixture is warmed to remove excess halogen reactant and by-product hydrogen halide, e.g., phosgene and hydrogen chloride, which are neutralized in appropriate scrubbers connected to the reaction vessel. Further warming of the haloformate in the presence of the carbon catalyst to haloformate decomposition temperatures results in conversion of the haloformate to the corresponding halide. This technique allows preparation of the halogen-capped organic compound in one step using one reaction vessel. Such technique enhances removal of the halogen reactant and by-product hydrogen halide, e.g., phosgene and hydrogen chloride from the organic halide product, eliminates the loss of product resulting from transfers between vessels, and avoids isolation of the intermediate haloformate product, which may also result in the loss of product. A one step process also reduces the amount of equipment required to practice the process. In a modification of this embodiment, the carbon catalyst is added to the haloformate product following its preparation and elimination of any residual halogen reactant, e.g., phosgene.

The process of the present invention is more particularly described in the following examples which are intended as illustrative only since numerous modifications and variations therein will be apparent to those skilled in the art.

EXAMPLE 1

A dry 100 milliliter reaction flask equipped with a stirrer, thermometer, Therm-O-Watch ® temperature controller, drying tube with calcium sulfate and heating mantle was charged with 48.47 grams of a liquid chloroformate having the general formula, $R_1(OCH_2CH_2)_3OC(O)Cl$, wherein $R_1$ was an alkyl radical having an average of 12 to 15 carbon atoms. The reaction flask was then charged with 1.02 grams (2.1 weight %) of granular Darco ® activated carbon (20–40 mesh). Heat was applied to the reaction flask and gas evolution was observed to begin at a reaction mixture temperature of about 90° C. Heating of the reaction mixture continued with consequent gas evolution, until the temperature of the reaction mixture was about 142° C. A sample of the reaction mixture was taken at 0.5, 1, 1.5, 2, 4 and 6 hours during which time period, the temperature of the reaction was held at 140–142° C., by temperature controller. The six-hour sample was taken after separating the carbon catalyst by filtration. Analysis of the samples by infrared analysis indicated that decomposition of the chloroformate proceeded progressively during the heating period. Calculations based on an analysis of the six-hour sample indicated about 2.86 percent of chloroformate still present in the product. It was concluded that a higher amount of catalyst was required to achieve more complete conversion of the chloroformate to the chloride. The product was nearly colorless.

EXAMPLE 2

A dry two hundred milliliter three-necked flask equipped with thermometer, Teflon ® coated stirring bar, Therm-O-Watch ® temperature controller, and heating mantle was charged with 100 grams of a liquid chloroformate having the general formula, $R_5(OCH_2CH_2)_7OC(O)Cl$, wherein $R_5$ was an alkyl radical having an average of 13 to 14 carbon atoms, and an initial temperature of about 44° C. To the flask was added 3 grams of granular activated carbon catalyst. Heat was applied to the reaction flask and gas evolution was observed at 110° C. Heating of the reaction mixture continued with consequent gas evolution until the temperature reached 140° C. The liquid in the flask was held at 140° C. for 6 hours. The material in the flask was filtered through a 0.45 micron millipore filter. It was colorless to slightly yellow in color. Analysis of a sample of the material found it to contain about 2.98 percent of the chloroformate.

EXAMPLE 3

A dry two hundred milliliter, three-necked round bottom flask equipped with thermometer, Teflon ® coated stirring bar, water-cooled condenser and drying tube, heating mantle and Therm-O-Watch ® temperature controller was charged with 100 grams of 2-ethylhexyl chloroformate and 3 grams of granular activated carbon catalyst. Heat was applied to the reaction flask and the temperature was increased from an initial level of 20° C. to 120° C. at which temperature vigorous gas evolution was observed. The reaction mixture was maintained at 120° C., for 7 hours and 40 minutes and for 4 hours at 140° C. Samples of the reaction mixture taken during these periods followed the conversion of 2-ethylhexyl chloroformate to 2-ethylhexyl chloride. The reaction mixture was cooled and filtered through a millipore filter. The liquid product had a very slight yellow color. The APHA color was reported as 25. Gas chromatographic analysis of the product detected no starting chloroformate. The product was about 88 percent 2-ethylhexyl chloride.

While the invention has been described in detail with respect to certain embodiments thereof, it is to be understood that the invention is not intended to be limited to such details except as and insofar as they appear in the appended claims.

I claim:

1. A method for preparing the corresponding halide of an organic haloformate of the general formula, $$R_1(OR')_nOC(O)X$$

wherein X is chlorine or bromine, $R_1$ is selected from the group consisting of $C_1$-$C_{30}$ alkyl, $C_5$-$C_6$ cycloalkyl, $C_1$-$C_4$ alkyl substituted $C_5$-$C_6$ cycloalkyl, phenyl, alkyl substituted phenyl of the general formula, $(R_2)_bPh$—, wherein Ph is phenylene, $R_2$ is $C_1$-$C_{18}$ alkyl and b is an integer of from 1 to 3, phen($C_1$-$C_{18}$) alkyl and $C_1$-$C_{18}$ alkyl-substituted phen($C_1$-$C_{18}$) alkyl having a total of from 7 to about 28 carbon atoms, R'is the substituted ethylene group, —$CH_2$—$CH(R'')$—, wherein R'' is selected from hydrogen, methyl, ethyl and mixtures thereof, and n is a number from 0 to 40, provided that when $R_1$ is phenyl or alkyl substituted phenyl, n is at least 1, which comprises heating said haloformate for a time and at temperatures sufficient to convert the haloformate to the corresponding halide in the presence of a catalytic amount of an activated carbon catalyst.

2. The method of claim 1 wherein the temperature at which the conversion is performed is from about 90° C. to about 150° C.

3. The method of claim 1 wherein the period of time during which the haloformate is heated is between 0.5 and 6 hours.

4. The method of claim 1 wherein the amount of activated carbon catalyst used is between 0.5 and 5 weight percent, based on the weight of the haloformate.

5. The method of claim 1 wherein the organic haloformate is an organic chloroformate and the corresponding halide is a chloride.

6. The method of claim 5 wherein the amount of catalyst used is between about 1 and about 3 weight percent, based on the weight of the chloroformate and the temperature at which the conversion is performed is between 100° C. and 140° C.

7. The method of claim 6 wherein the period of time during which the chloroformate is heated is between 1 and 3 hours.

8. The method of claim 1 wherein the organic haloformate is represented by the general formula, $R_1(OR'-)_nOC(O)X$, wherein $R_1$ is a $C_1$-$C_{30}$ alkyl, X is chlorine and R'is the ethylene group, —$CH_2$—$CH_2$—, and n is a number from 0 to 40.

9. The method of claim 8 wherein $R_1$ is a $C_8$-$C_{18}$ alkyl and n is a number from 2 to 20.

10. The method of claim 8 wherein the amount of catalyst used is between about 0.5 and 5 weight percent, based on the weight of the haloformate, and the temperature at which the conversion is performed is from about 90° C. to 150° C.

11. The method of claim 9 wherein the amount of catalyst used is between about 1 and 3 weight percent, based on the weight of haloformate, and the temperature at which the conversion is performed is between 100° C. and 140° C.

12. The method of claim 10 wherein conversion of the organic haloformate to the corresponding organic halide is conducted in the absence of a solvent for the haloformate.

* * * * *